(12) United States Patent
Nakatani

(10) Patent No.: US 11,066,422 B2
(45) Date of Patent: Jul. 20, 2021

(54) METHOD OF PRODUCING CYCLOALKYL(TRIFLUOROMETHYL) BENZENE

(71) Applicant: Toray Fine Chemicals Co., Ltd., Tokyo (JP)

(72) Inventor: Jiro Nakatani, Tokai (JP)

(73) Assignee: Toray Fine Chemicals Co., Ltd., Tokyo (JP)

( * ) Notice: Subject to any disclaimer, the term of this patent is extended or adjusted under 35 U.S.C. 154(b) by 28 days.

(21) Appl. No.: 16/613,300

(22) PCT Filed: Jul. 6, 2018

(86) PCT No.: PCT/JP2018/025696
§ 371 (c)(1),
(2) Date: Nov. 13, 2019

(87) PCT Pub. No.: WO2019/013126
PCT Pub. Date: Jan. 17, 2019

(65) Prior Publication Data
US 2021/0053992 A1    Feb. 25, 2021

(30) Foreign Application Priority Data

Jul. 13, 2017   (JP) .............................. JP2017-137129

(51) Int. Cl.
| C07C 17/278 | (2006.01) |
| C07C 17/263 | (2006.01) |
| C07F 3/02 | (2006.01) |
| C07C 17/26 | (2006.01) |
| C07C 22/08 | (2006.01) |
| B01J 37/16 | (2006.01) |
| B01J 23/745 | (2006.01) |
| B01J 23/75 | (2006.01) |

(52) U.S. Cl.
CPC ............... *C07F 3/02* (2013.01); *C07C 17/26* (2013.01); *C07C 17/2632* (2013.01); *C07C 17/278* (2013.01); *C07C 22/08* (2013.01); *B01J 23/745* (2013.01); *B01J 23/75* (2013.01); *B01J 37/16* (2013.01); *C07C 2601/08* (2017.05)

(58) Field of Classification Search
None
See application file for complete search history.

(56) References Cited

U.S. PATENT DOCUMENTS

| 2007/0123734 A1 | 5/2007 | Nakamura et al. |
| 2011/0152523 A1 | 6/2011 | Nakamura et al. |
| 2012/0295947 A1 | 11/2012 | Montalban et al. |
| 2017/0159088 A1* | 6/2017 | Montalban .............. C12P 17/10 |

FOREIGN PATENT DOCUMENTS

| EP | 1724248 A1 | 11/2006 |
| JP | 2011-001369 | 1/2011 |
| JP | 2013-518106 | 5/2013 |
| JP | 2016-121121 | 7/2016 |
| WO | 2010/001640 | 1/2010 |
| WO | 2010/011316 | 1/2010 |
| WO | 2013/113915 | 8/2013 |

OTHER PUBLICATIONS

Tanaka, Yoshie et al., "Development of efficient structure conversion reaction of aromatic compounds aiming not to use rare-metal," *Research reports of Industrial Technology Center of of Wakayamaa*, 2011, p. 25, including an English Abstract.

Nakamura, M. et al., "Iron-Catalyzed Cross-Coupling of Primary and Secondary Alkyl Halides with Aryl Grignard Reagents, " *Journal of the American Chemical Society.* 126 (12): pp. 3686-3687. Mar. 4, 2004. https://pubs.acs.org/doi/abs/10.1021/ja049744t (Abstract Only).

Ghorai, S. et al., "Cross-Coupling of Non-activated Chloroalkanes with Aryl Grignard Reagents in the Presence of Iron/N-Heterocyclic Carbene Catalysts."*Organic Letters.* 14(4): pp. 1066-1069. Jan. 30, 2012. https://doi.org/10.1021/ol2031729 (Abstract Only).

Yamaguchi, Y. et al., "Synthesis of Iron (III) Complex Bearing Tridentate β-Aminoketortaro Ligand: Application to Iron-catalyzed Cross-Coupling Reaction of Arylmagnesium Bromides with Alkyl Halides." *Chemistry Letters.* 40(9): pp. 983-985. Sep. 5, 2011. https://doi.org/10.1246/c1.2011.983.

Hatakeyama, T. et al., "Kumada-Tamao-Corriu Coupling of Alkyl Halides Catalyzed by an Iron-Bisphosphine Complex," *Chemistry Letters.* 40(9): pp. 1030-1032. Sep. 5, 2011. https://doi.org/10.1246/cl.2011.1030.

Czaplik, W. et al., "Domino Iron-Catalysis: Direct Aryl-Alkyl Cross-Coupling" *Angewandte Chemie International Edition.* 48: pp. 607-610. 2009. https://doi.org/10.1002/anie.200804434 (Abstract Only).

Li, Z. et al., "Iron-mediated inter- and Intramolecular reductive cross-coupling of unactivated alkyl chlorides with aryl bromides," *Organic Biomolecular Chemistry.* 14(12): pp. 3314-3321. 2016. https://pubs.rsc.org/en/content/articlelanding/2016/ob/c6ob00247a#!divAbstract (Abstract Only).

Hedström, A. et al., "Iron-Catalyzed Coupling of Aryl Grignard Reagents with Alkyl Halides: A Competitive Hammett Study." *Chemistry: A European Journal.* 17: pp. 11991-11993. 2011. https://doi.org/10.1002/chem.201100467.

Sengupta, D. et al., "An Efficient Scale-Up Process for the Preparation of the APD334 Precursor 4-Chloromethyl-1-cyclopentyl-2-(trifluoromethyl)benzene", *Organic Process Research & Development*, Mar. 25, 2015, 19 (6), 618-623.

(Continued)

*Primary Examiner* — Medhanit W Bahta
(74) *Attorney, Agent, or Firm* — DLA Piper LLP (US)

(57) ABSTRACT

An industrially excellent production method for cycloalkyl (trifluoromethyl)benzene is free of complicated steps, small in the number of steps, and high in production efficiency. Cycloalkyl(trifluoromethyl)benzene is produced by reacting a halogen-substituted trifluoromethyl benzene with magnesium metal to produce a Grignard reagent and cross-coupling the Grignard reagent with a cycloalkyl halide in the presence of an iron salt or a cobalt salt at a reaction temperature of 60° C. to 80° C.

2 Claims, No Drawings

(56) References Cited

OTHER PUBLICATIONS

Communication dated Nov. 9, 2020, of counterpart European Application No. 188832867.8.
The Extended European Search Report dated Feb. 26, 2021, of counterpart European Application No. 18832867.8.

* cited by examiner

METHOD OF PRODUCING CYCLOALKYL(TRIFLUOROMETHYL)BENZENE

TECHNICAL FIELD

This disclosure relates to a method of producing cycloalkyl(trifluoromethyl)benzene and more specifically relates to an industrially excellent method of producing cycloalkyl(trifluoromethyl)benzene.

BACKGROUND

Cycloalkyl(trifluoromethyl)benzene is a useful compound in the fields of fine chemicals, medical and agrochemical materials, resin and plastic materials, electronic information materials, and optical materials.

WO 2010/011316 discloses a method of producing cycloalkyl(trifluoromethyl)benzene in which 1-bromo-2-(trifluoromethyl)benzene is lithiated with butyl lithium and then reacted with cyclopentanone to produce 1-(2-(trifluoromethyl)phenyl)cyclopentanol. Furthermore, this is dehydrated and hydrogenated to provide 1-cyclopentyl-2-(trifluoromethyl)benzene.

WO 2013/113915 discloses a method in which 1-bromo-2-(trifluoromethyl)benzene is subjected to Grignard exchange reaction with isopropyl magnesium bromide and reacted with cyclohexanone to produce 1-(2-(trifluoromethyl)phenyl)cyclohexanol. Furthermore, this is dehydrated and hydrogenated to provide 1-cyclohexyl-2-(trifluoromethyl)benzene.

Journal of American Chemistry Society, 2004, 126, 3686-3687 discloses a method in which iron chloride having coordinated N,N,N',N'-tetramethyl ethylenediamine is used as a catalyst to perform a cross-coupling reaction between 4-(trifluoromethyl)phenyl magnesium bromide and cyclohexyl bromide at a low temperature of −78 to 0° C.

Organic Letters, Vol. 14, No. 4, 1066-1069 (2012), Chemistry Letters, 2011, 40, 983-985 and Chemistry Letters, 2011, 40, 1030-1032 disclose methods in which iron chloride having a specific ligand is used as a catalyst to perform a cross-coupling reaction between a phenylmagnesium halide and cycloalkyl halide.

The method described in WO 2010/011316, however, requires a multi-stage reaction step in which the lithiation reaction performed at an extremely low temperature of −78° C. is followed by a dehydration reaction and a hydrogenation reaction.

The method described in WO 2013/113915 uses a dilute solution of isopropylmagnesium bromide and therefore also requires a multi-stage reaction step in which the Grignard exchange reaction, which is not high in high productivity, is followed by a dehydration reaction and a hydrogenation reaction.

The resulting products of cycloalkyl(trifluoromethyl)benzene are expensive since those methods require a complicated multi-stage reaction step including a low productivity stage for a reaction in a very cold or dilute solution.

The method in Journal of American Chemistry Society, 2004, 126, 3686-3687, which uses iron chloride having coordinated N,N,N',N'-tetramethyl ethylenediamine, is expensive, as a catalyst to perform a cross-coupling reaction between 4-(trifluoromethyl)phenyl magnesium bromide and cyclohexyl bromide at a low temperature of −78 to 0° C., produces 1-cyclohexyl-4-(trifluoromethyl)benzene with a yield of 67%. However, that method uses an excessive 1.5 equivalents of 4-(trifluoromethyl)phenyl magnesium bromide, and the yield is a low value of 44% in terms of 4-(trifluoromethyl)phenyl magnesium bromide.

The ligands disclosed in Organic Letters, Vol. 14, No. 4, 1066-1069 (2012), Chemistry Letters, 2011, 40, 983-985 or Chemistry Letters, 2011, 40, 1030-1032 are expensive or actually unavailable, representing industrial disadvantages, and they include no descriptions regarding the possibility of applying cycloalkyl(trifluoromethyl)benzene.

There are industrial problems with the use of these aforementioned methods of producing cycloalkyl(trifluoromethyl)benzene and a low-price method of producing cycloalkyl(trifluoromethyl)benzene is needed.

It could therefore be helpful to provide an industrially excellent method of producing cycloalkyl(trifluoromethyl)benzene that is free of complicated steps, small in the number of steps, and high in production efficiency.

SUMMARY

I thus provide:

A method of producing cycloalkyl(trifluoromethyl)benzene including a step of reacting a halogen-substituted trifluoromethyl benzene as represented by general formula (1) with magnesium metal to produce a Grignard reagent and a step of cross-coupling the Grignard reagent with a cycloalkyl halide in the presence of an iron salt or a cobalt salt at a reaction temperature of 60° C. to 80° C. to produce cycloalkyl(trifluoromethyl)benzene as represented by general formula (2).

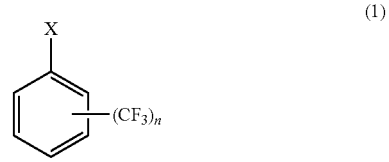

(1)

where X is Cl or Br, and n is 1 or 2

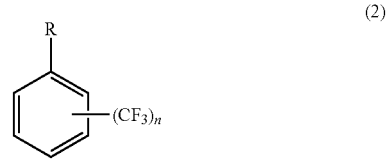

(2)

where R is one selected from the group consisting of cyclopropyl, cyclobutyl, cyclopentyl, cyclohexyl, and cycloheptyl, and n is 1 or 2.

The method of producing cycloalkyl(trifluoromethyl)benzene uses halogen-substituted trifluoromethyl benzene, which is low in price, as starting material. Furthermore, I provide an industrially excellent production method that can produce cycloalkyl(trifluoromethyl)benzene efficiently without using expensive materials by producing a Grignard reagent as an intermediate and cross-coupling the Grignard reagent with a cycloalkyl halide in the presence of an iron salt or a cobalt salt.

The cycloalkyl(trifluoromethyl)benzene produced by the method of producing cycloalkyl(trifluoromethyl)benzene can be used as fine chemicals, medical and agrochemical materials, resin and plastic materials, electronic information materials, and optical materials.

DETAILED DESCRIPTION

My methods are described in detail below.

The method of producing cycloalkyl(trifluoromethyl)benzene uses halogen-substituted trifluoromethyl benzene as represented by general formula (1) as starting material.

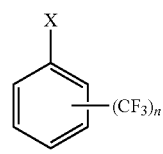

(1)

where X is Cl or Br, and n is 1 or 2.

Specific examples of the halogen-substituted trifluoromethyl benzene include o-chlorobenzotrifluoride, o-bromobenzotrifluoride, m-chlorobenzotrifluoride, m-bromobenzotrifluoride, p-chlorobenzotrifluoride, p-bromobenzotrifluoride, 1-chloro-3,5-bis(trifluoromethyl)benzene, and 1-bromo-3,5-bis(trifluoromethyl)benzene.

The Cl or Br atom in the halogen-substituted trifluoromethyl benzene is reacted with magnesium metal to convert it into a Grignard reagent. The conversion reaction into a Grignard reagent can be achieved by a generally known conversion reaction.

Magnesium metal is available in the form of powder or shavings, but preferably in the form of shavings from the viewpoint of handleability. The magnesium metal component to be fed preferably accounts for 0.8 to 3 moles relative to 1 mole of the halogen-substituted trifluoromethyl benzene component used as starting material.

It is preferable to add iodine, bromine, or a low-priced compound containing either of them to the solvent containing magnesium metal to remove the surface oxide film from the magnesium metal to ensure an increased reactivity. Preferable examples of such a compound include methyl iodide, methyl bromide, ethyl iodide, and ethyl bromide.

The reaction for conversion into a Grignard reagent is performed in a dehydrated system. For this, a solvent dehydrated in advance may be used for the reaction, or a low-priced Grignard reagent product may be added to the solvent before the reaction to remove water from the solvent.

A solvent that can promote the reaction efficiently is used for formation of a Grignard reagent. The solvent used for formation of a Grignard reagent is preferably an ether based solvent suitable for Grignard reagent formation. Specific examples of such a solvent include diethyl ether, diisopropyl ether, tetrahydrofuran, N,N-dimethyl formamide, N,N-dimethyl acetamide, N-methyl pyrrolidone, 1,3-dioxane, 1,4-dioxane, cyclopropyl methyl ether, methyl-tertiary butyl ether, ethylene glycol dimethyl ether, diethylene glycol dimethyl ether, triethylene glycol dimethyl ether, tetraethylene glycol dimethyl ether, benzene, toluene, and xylene. Particularly preferable ones include diethyl ether, diisopropyl ether, tetrahydrofuran, 1,3-dioxane, 1,4-dioxane, cyclopropyl methyl ether, and methyl-tertiary butyl ether.

An appropriate amount of the solvent is preferably determined on the basis of the solubility of the halogen-substituted trifluoromethyl benzene or Grignard reagent, slurry concentration, and properties of the reaction liquid. The solvent to be used accounts for 1 to 100 moles relative to 1 mole of the halogen-substituted trifluoromethyl benzene component. A content of less than 1 mole may lead to a decreased yield of Grignard reagent, whereas a content of more than 100 moles may lead to a decreased productivity, resulting in an uneconomical process.

For the Grignard reagent production, it is preferable for LiCl (lithium chloride) to coexist when a halogen-substituted trifluoromethyl benzene as represented by general formula (1) is reacted with magnesium metal to convert it into a Grignard reagent. This is because the coexistence of LiCl promotes the formation of the Grignard reagent to ensure a high yield in the subsequent cross-coupling reaction with a cycloalkyl halide.

For the conversion into a Grignard reagent, the LiCl to be used preferably accounts for 0.01 to 3 moles relative to 1 mole of the halogen-substituted trifluoromethyl benzene component. The content is more preferably 0.05 to 1 mole. If the LiCl accounts for 0.01 to 3 moles relative to 1 mole of the halogen-substituted trifluoromethyl benzene, the Grignard reagent will be produced more quickly and the LiCl will be completely dissolved in the reaction system.

Specific examples of the cycloalkyl halide used for the reaction with the Grignard reagent include chlorocyclopropyl, bromocyclopropyl, chlorocyclobutyl, bromocyclobutyl, chlorocyclopentyl, bromocyclopentyl, chlorocyclohexyl, bromocyclohexyl, chlorocycloheptyl, and bromocycloheptyl. Preferred ones include bromocyclopropyl, bromocyclobutyl, bromocyclopentyl, bromocyclohexyl, and bromocycloheptyl.

The cycloalkyl halide to be fed preferably accounts for 0.5 to 10 moles, more preferably 1 to 2 moles, relative to 1 mole of the halogen-substituted trifluoromethyl benzene. A content of less than 0.5 mole will allow a compound to form as a result of the homocoupling between Grignard reagent molecules, leading to a decrease in yield. If it is more than 10 moles, unreacted molecules of the cycloalkyl halide will remain to decrease the productivity, possibly leading to an increased load on the separation between the unreacted cycloalkyl halide molecules and cycloalkyl(trifluoromethyl)benzene.

The Grignard reagent is reacted with a cycloalkyl halide in the presence of an iron salt or a cobalt salt. Preferred iron salts include ferrous chloride, ferric chloride, iron acetate, iron acetylacetonate, and preferred cobalt salts include cobalt chloride and cobalt acetylacetonate.

The iron salt or cobalt salt to be fed preferably accounts for 0.005 to 1.0 mole, more preferably 0.01 to 0.5 mole, relative to 1 mole of the Grignard reagent of halogen-substituted trifluoromethyl benzene.

The iron salt or cobalt salt to be used is preferably subjected to reduction treatment before the Grignard reagent is allowed to react with a cycloalkyl halide. Specifically, the iron salt or cobalt salt is dissolved in the reaction system and then a reducing agent is added, which works to alter the iron salt or cobalt salt into a reduced state. Specific examples of such a reducing agent include lithium aluminum hydride, sodium boron hydride, sulfites, hydrazine, diisobutylaluminum hydride, oxalic acid, formic acid, and Grignard reagents having 1 to 4 carbon atoms, of which Grignard reagents having 1 to 4 carbon atoms are preferred. Examples of the Grignard reagents having 1 to 4 carbon atoms include methyl magnesium bromide, methyl magnesium chloride, ethyl magnesium bromide, ethyl magnesium chloride, isopropyl magnesium bromide, isopropyl magnesium chloride, tertiary-butyl magnesium chloride, and tertiary-butyl magnesium bromide.

There are no specific limitations on the timing of the reduction treatment of the iron salt or cobalt salt as long as it is performed before reacting the Grignard reagent with a cycloalkyl halide. For example, an iron salt or a cobalt salt may be added to a solution containing a cycloalkyl halide, followed by adding a reducing agent to achieve reduction treatment, or a reducing agent may be added to a solution containing an iron salt or a cobalt salt to achieve reduction treatment, followed by feeding the liquid into a solution of a cycloalkyl halide.

The reducing agent to be added preferably accounts for 0.5 to 30 moles, preferably 1.0 to 15 moles, relative to 1 mole of the iron salt or cobalt salt.

The temperature for the reduction treatment of the iron salt or cobalt salt is preferably 20° C. to 80° C., and more preferably 40° C. to 60° C.

It is preferable that a N-methyl pyrrolidone is added, in combination with the iron salt or cobalt salt, to the cross-coupling reaction system in which the Grignard reagent is to be reacted with a cycloalkyl halide. This is because the N-methyl pyrrolidone will coordinate with the iron salt or cobalt salt to form a preferred catalyst for the reaction between the Grignard reagent and cycloalkyl halide to improve the yield of cycloalkyl(trifluoromethyl)benzene.

The N-methyl pyrrolidone to be added preferably accounts for 0.5 to 20 moles relative to 1 mole of the iron salt or cobalt salt, and the N-methyl pyrrolidone may be used as the solvent for the reaction between the Grignard reagent and cycloalkyl halide.

A solvent may be used for the cross-coupling reaction between the Grignard reagent and cycloalkyl halide. The solvent to be used is preferably one that promotes the reaction efficiently rather than impeding it. Specific examples of such a solvent include diethyl ether, diisopropyl ether, tetrahydrofuran, N,N-dimethyl formamide, N,N-dimethyl acetamide, N-methyl pyrrolidone, cyclopropyl methyl ether, methyl-tertiary butyl ether, ethylene glycol dimethyl ether, diethylene glycol dimethyl ether, triethylene glycol dimethyl ether, tetraethylene glycol dimethyl ether, benzene, toluene, and xylene. Of these, particularly preferred ones include N-methyl pyrrolidone, tetrahydrofuran, cyclopropyl methyl ether, benzene, toluene, xylene, and mesitylene. N-methyl pyrrolidone is still more preferred.

The solvent to be used for the cross-coupling reaction preferably accounts for 0.05 to 50 parts by weight relative to 1 part by weight of the Grignard reagent of the halogen-substituted trifluoromethyl benzene. If the content of the solvent is less than 0.05 part by weight, it will be so difficult to remove the heat of reaction that runaway reaction can sometimes occur. A content of more than 50 parts by weight can sometimes lead to a poor productivity.

The reaction between a Grignard reagent and a cycloalkyl halide may be carried out by pouring a solution containing the cycloalkyl halide in a solution containing the Grignard reagent or pouring a solution containing the Grignard reagent in a solution containing the cycloalkyl halide. It is preferable that the iron salt or cobalt salt is added in advance to the solution containing a cycloalkyl halide. To prevent a sudden exothermic reaction or runaway reaction, it is preferable to control the pouring speed of the solution by adding it continuously over a long period or intermittently in parts so that the temperature in the reaction system stays in a set range. A pouring period of 0.5 to 6 hours is preferred.

The cross-coupling reaction between a Grignard reagent and a cycloalkyl halide is performed at a reaction temperature of 60° C. to 80° C. If the reaction temperature is less than 60° C., the homocoupling reaction between molecules of the Grignard reagent will occur preferentially as a side reaction to cause the production of bis(trifluoromethyl) biphenyl in a large amount. If it is more than 80° C., the Grignard reagent will be heat-decomposed before starting to react, leading to the production of benzotrifluoride as a by-product. The reaction temperature is preferably 65° C. to 75° C.

The reaction period of the cross-coupling reaction between a Grignard reagent and a cycloalkyl halide is normally 0.5 to 40 hours, preferably 1.0 to 5 hours, at 60° C. to 80° C. after mixing the whole amount of the solution containing a Grignard reagent solution and a cycloalkyl halide.

It is preferable that the end of the cross-coupling reaction between a Grignard reagent and a cycloalkyl halide is followed by adding water, acidic water, or alkaline water to inactivate the reaction liquid while removing the resulting magnesium halide in the water phase. Then, cycloalkyl (trifluoromethyl)benzene can be isolated from the resulting oil phase.

The resulting cycloalkyl(trifluoromethyl)benzene is represented by general formula (2):

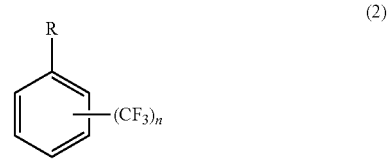

where R is one selected from the group consisting of cyclopropyl, cyclobutyl, cyclopentyl, cyclohexyl, and cycloheptyl, and n is 1 or 2.

Examples of the cycloalkyl(trifluoromethyl)benzene produced by the production method include 1-cyclopentyl-2-trifluoromethyl benzene, 1-cyclohexyl-2-trifluoromethyl benzene, 1-cyclopentyl-4-trifluoromethyl benzene, 1-cyclohexyl-4-trifluoromethyl benzene, 1-cyclopentyl-3-trifluoromethyl benzene, and 1-cyclohexyl-3-trifluoromethyl benzene. Preferred ones include 1-cyclopentyl-2-trifluoromethyl benzene and 1-cyclohexyl-2-trifluoromethyl benzene.

Useful methods of isolating the intended cycloalkyl(trifluoromethyl)benzene from the reaction liquid include distillation, crystallization, extraction, column separation using silica and the like, and simulated moving bed adsorption separation, and a plurality of methods may be combined. For example, there are various preferred distillation techniques including simple distillation, rectification, vacuum distillation, and atmospheric distillation, of which vacuum distillation is more preferred.

The cycloalkyl(trifluoromethyl)benzene compounds produced by the production method are useful in a variety of fields and therefore, making them industrially available with high efficiency is of great significance.

EXAMPLES

My methods are further described in more detail below with reference to Examples. The reagents used herein are of an extra pure level according to the manufacturer's grade standards.

Example 1

In a 200 ml four-necked flask equipped with a thermometer, 75.0 g of tetrahydrofuran (abbreviated as THF) (1.04 mole, manufactured by Nacalai Tesque Inc.), 5.1 g of magnesium powder (0.208 mole, manufactured by Chuo Kosan Co., Ltd.), and 2.5 g of LiCl (0.06 mole, manufactured by Nacalai Tesque Inc.) were fed and stirred while filling the container with nitrogen. Then 0.5 g of a 1 mol/L THF solution of ethyl magnesium bromide (manufactured by Tokyo Chemical Industry Co., Ltd.) was added to this to remove moisture out of the system. Subsequently, 0.44 g of ethyl bromide (0.004 mole, manufactured by Wako Pure Chemical Industries, Ltd.) was added. Stirring was performed for a while and heat generation was confirmed. Then, while maintaining the reaction liquid temperature at 45° C. to 50° C., 36.1 g of o-chlorobenzotrifluoride (0.2 mole, manufactured by Wako Pure Chemical Industries, Ltd.) was dropped gradually. After the end of dropping, stirring was performed at 45° C. for 5 hours for aging. After the end of aging, 10.8 g of toluene was added to prepare a Grignard reagent solution.

Next, in a 300 ml four-necked flask equipped with a thermometer, 61.4 g of THF (0.85 mole, manufactured by Nacalai Tesque Inc.), 35.8 g of cyclopentyl bromide (1.2 moles per mole of o-chlorobenzotrifluoride, manufactured by Wako Pure Chemical Industries, Ltd.), and 1.6 g of ferric chloride (0.05 mole per mole of o-chlorobenzotrifluoride, manufactured by Wako Pure Chemical Industries, Ltd.) were fed and, while filling the container with nitrogen, heated and stirred in a water bath. The aforementioned Grignard reagent solution was dropped while controlling so that the reaction liquid temperature is maintained at 70° C. After the completion of the dropping of the Grignard reagent solution, aging was performed at 70° C. for 2 hours.

After the end of aging, the reaction liquid was returned to room temperature, and 42.4 g of a 5% aqueous hydrogen chloride solution was dropped gradually in a water bath. After the end of dropping, the liquid was stirred for 1 hour and left to stand for liquid separation to obtain an oil phase containing 1-cyclopentyl-2-(trifluoromethyl)benzene.

The oil phase obtained was analyzed by gas chromatography (GC), and results showed that the reaction yield of 1-cyclopentyl-2-(trifluoromethyl)benzene was 57.7% (on the basis of o-chlorobenzotrifluoride fed as starting material).

Example 2

In the procedure carried out in Example 1, except for dropping the Grignard reagent solution at a temperature of 75° C. instead of 70° C. and performing aging at a temperature of 75° C. instead of 70° C. after the completion of dropping of the Grignard reagent solution, the same reaction procedure as in Example 1 was performed.

The oil phase obtained was analyzed by gas chromatography, and results showed that the reaction yield of 1-cyclopentyl-2-(trifluoromethyl)benzene was 60.0% (on the basis of o-chlorobenzotrifluoride fed as starting material).

Comparative Example 1

In the procedure carried out in Example 1, except for dropping the Grignard reagent solution at a temperature of 10° C. instead of 70° C. and performing aging at a temperature of 10° C. instead of 70° C. after the completion of dropping of the Grignard reagent solution, the same reaction procedure as in Example 1 was performed.

The oil phase obtained was analyzed by gas chromatography, and results showed that the reaction yield of 1-cyclopentyl-2-(trifluoromethyl)benzene was 10.0% (on the basis of o-chlorobenzotrifluoride fed as starting material).

Comparative Example 2

In the procedure carried out in Example 1, except for dropping the Grignard reagent solution at a temperature of 50° C. instead of 70° C. and performing aging at a temperature of 50° C. instead of 70° C. after the completion of dropping of the Grignard reagent solution, the same reaction procedure as in Example 1 was performed.

The oil phase obtained was analyzed by gas chromatography, and results showed that the reaction yield of 1-cyclopentyl-2-(trifluoromethyl)benzene was 37.4% (on the basis of o-chlorobenzotrifluoride fed as starting material).

Comparative Example 3

In the procedure carried out in Example 1, except for dropping the Grignard reagent solution at a temperature of 90° C. instead of 70° C. and performing aging at a temperature of 90° C. instead of 70° C. after the completion of dropping of the Grignard reagent solution, the same reaction procedure as in Example 1 was performed.

The oil phase obtained was analyzed by gas chromatography, and results showed that the reaction yield of 1-cyclopentyl-2-(trifluoromethyl)benzene was 21.3% (on the basis of o-chlorobenzotrifluoride fed as starting material).

Example 3

In the procedure carried out in Example 1, except for adding 1.3 g of ferrous chloride (0.05 mole per mole of o-chlorobenzotrifluoride, manufactured by Wako Pure Chemical Industries, Ltd.) instead of 1.6 g of ferric chloride (0.05 mole per mole of o-chlorobenzotrifluoride, manufactured by Wako Pure Chemical Industries, Ltd.), the same reaction procedure as in Example 1 was carried out.

The oil phase obtained was analyzed by gas chromatography, and results showed that the reaction yield of 1-cyclopentyl-2-(trifluoromethyl)benzene was 55.6% (on the basis of o-chlorobenzotrifluoride fed as starting material).

Example 4

In the procedure carried out in Example 1, except for adding 3.5 g of iron acetylacetonate (0.05 mole per mole of o-chlorobenzotrifluoride, manufactured by Wako Pure Chemical Industries, Ltd.) instead of 1.6 g of ferric chloride (0.05 mole per mole of o-chlorobenzotrifluoride, manufactured by Wako Pure Chemical Industries, Ltd.), the same reaction procedure as in Example 1 was carried out.

The oil phase obtained was analyzed by gas chromatography, and results showed that the reaction yield of 1-cyclopentyl-2-(trifluoromethyl)benzene was 53.4% (on the basis of o-chlorobenzotrifluoride fed as starting material).

Example 5

In the procedure carried out in Example 1, except for adding 1.3 g of cobalt (II) chloride (0.05 mole per mole of o-chlorobenzotrifluoride, manufactured by Wako Pure Chemical Industries, Ltd.) instead of 1.6 g of ferric chloride (0.05 mole per mole of o-chlorobenzotrifluoride, manufactured by Wako Pure Chemical Industries, Ltd.), the same reaction procedure as in Example 1 was carried out.

The oil phase obtained was analyzed by gas chromatography, and results showed that the reaction yield of 1-cyclopentyl-2-(trifluoromethyl)benzene was 51.3% (on the basis of o-chlorobenzotrifluoride fed as starting material).

Comparative Example 4

In the procedure carried out in Example 1, except for adding 2.2 g of palladium acetate (0.05 mole per mole of o-chlorobenzotrifluoride, manufactured by Wako Pure Chemical Industries, Ltd.) instead of 1.6 g of ferric chloride (0.05 mole per mole of o-chlorobenzotrifluoride, manufactured by Wako Pure Chemical Industries, Ltd.), the same reaction procedure as in Example 1 was carried out.

The oil phase obtained was analyzed by gas chromatography, and results showed that 1-cyclopentyl-2-(trifluoromethyl)benzene was not produced.

Comparative Example 5

In the procedure carried out in Example 1, except for adding 1.3 g of nickel chloride (0.05 mole per mole of o-chlorobenzotrifluoride, manufactured by Wako Pure Chemical Industries, Ltd.) instead of 1.6 g of ferric chloride (0.05 mole per mole of o-chlorobenzotrifluoride, manufactured by Wako Pure Chemical Industries, Ltd.), the same reaction procedure as in Example 1 was carried out.

The oil phase obtained was analyzed by gas chromatography, and results showed that the reaction yield of 1-cyclopentyl-2-(trifluoromethyl)benzene was 12.6% (on the basis of o-chlorobenzotrifluoride fed as starting material).

Comparative Example 6

In the procedure carried out in Example 1, except for adding 1.3 g of copper chloride (0.05 mole per mole of o-chlorobenzotrifluoride, manufactured by Wako Pure Chemical Industries, Ltd.) instead of 1.6 g of ferric chloride (0.05 mole per mole of o-chlorobenzotrifluoride, manufactured by Wako Pure Chemical Industries, Ltd.), the same reaction procedure as in Example 1 was carried out.

The oil phase obtained was analyzed by gas chromatography, and results showed that the reaction yield of 1-cyclopentyl-2-(trifluoromethyl)benzene was 0.5% (on the basis of o-chlorobenzotrifluoride fed as starting material).

Comparative Example 7

In the procedure carried out in Example 1, except for adding 1.3 g of manganese chloride (0.05 mole per mole of o-chlorobenzotrifluoride, manufactured by Wako Pure Chemical Industries, Ltd.) instead of 1.6 g of ferric chloride (0.05 mole per mole of o-chlorobenzotrifluoride, manufactured by Wako Pure Chemical Industries, Ltd.), the same reaction procedure as in Example 1 was carried out.

The oil phase obtained was analyzed by gas chromatography, and results showed that 1-cyclopentyl-2-(trifluoromethyl)benzene was not produced.

Example 6

In the cross-coupling reaction performed in Example 1, except for adding a cycloalkyl halide of 40.9 g of THF (0.57 mole, manufactured by Nacalai Tesque Inc.), 35.8 g of cyclopentyl bromide (1.2 moles per mole of o-chlorobenzotrifluoride, manufactured by Wako Pure Chemical Industries, Ltd.), and 1.6 g of ferric chloride (0.05 mole per mole of o-chlorobenzotrifluoride, manufactured by Wako Pure Chemical Industries, Ltd.) and also adding 20.5 g of N-methyl pyrrolidone (0.21 mole, manufactured by Nacalai Tesque Inc.) to the catalyst adjusting solution, the same reaction procedure as in Example 1 was carried out.

The oil phase obtained was analyzed by gas chromatography, and results showed that the reaction yield of 1-cyclopentyl-2-(trifluoromethyl)benzene was 72.4% (on the basis of o-chlorobenzotrifluoride fed as starting material).

Example 7

In the procedure carried out in Example 1, except for adding 61.4 g of N-methyl pyrrolidone (0.62 mole, manufactured by Nacalai Tesque Inc.) instead of 61.4 g of THF (0.85 mole, manufactured by Nacalai Tesque Inc.), the same reaction procedure as in Example 1 was carried out.

The oil phase obtained was analyzed by gas chromatography, and results showed that the reaction yield of 1-cyclopentyl-2-(trifluoromethyl)benzene was 74.3% (on the basis of o-chlorobenzotrifluoride fed as starting material).

Example 8

As in Example 7, in a 300 ml four-necked flask equipped with a thermometer, 61.4 g of N-methyl pyrrolidone (0.62 mole, manufactured by Nacalai Tesque Inc.), 35.8 g of cyclopentyl bromide (1.2 moles per mole of o-chlorobenzotrifluoride, manufactured by Wako Pure Chemical Industries, Ltd.), and 1.6 g of ferric chloride (0.05 mole per mole of o-chlorobenzotrifluoride, manufactured by Wako Pure Chemical Industries, Ltd.) were fed and, while filling the container with nitrogen, heated and stirred in a water bath, followed by performing reduction treatment by dropping 53 ml of a 1M THF solution of ethyl magnesium bromide (5.3 moles per mole of ferric chloride) while controlling to maintain a reaction liquid temperature of not more than 50° C. After the end of dropping, the Grignard reagent was dropped at 70° C. as in Example 7 to allow the reaction to proceed.

The oil phase obtained was analyzed by gas chromatography, and results showed that the reaction yield of 1-cyclopentyl-2-(trifluoromethyl)benzene was 79.6% (on the basis of o-chlorobenzotrifluoride fed as starting material).

Example 9

In the procedure carried out in Example 8, except for adding 107 ml (10.7 moles per mole of ferric chloride), instead of 53 ml, of a 1M THF solution of ethyl magnesium bromide, the same procedure as in Example 8 was carried out.

The oil phase obtained was analyzed by gas chromatography, and results showed that the reaction yield of 1-cyclopentyl-2-(trifluoromethyl)benzene was 85.3% (on the basis of o-chlorobenzotrifluoride fed as starting material).

Example 10

In the procedure carried out in Example 7, except for adding 1.3 g of cobalt (II) chloride (0.05 mole per mole of o-chlorobenzotrifluoride, manufactured by Wako Pure Chemical Industries, Ltd.) instead of 1.6 g of ferric chloride (0.05 mole per mole of o-chlorobenzotrifluoride, manufactured by Wako Pure Chemical Industries, Ltd.), the same reaction procedure as in Example 7 was carried out.

The oil phase obtained was analyzed by gas chromatography, and results showed that the reaction yield of 1-cyclopentyl-2-(trifluoromethyl)benzene was 63.3% (on the basis of o-chlorobenzotrifluoride fed as starting material).

Example 11

In the procedure carried out in Example 7, except for adding 61.4 g of N,N-dimethyl formamide (0.84 mole, manufactured by Nacalai Tesque Inc.) instead of 61.4 g of N-methyl pyrrolidone (0.62 mole, manufactured by Nacalai Tesque Inc.), the same reaction procedure as in Example 7 was carried out.

The oil phase obtained was analyzed by gas chromatography, and results showed that the reaction yield of 1-cyclopentyl-2-(trifluoromethyl)benzene was 62.2% (on the basis of o-chlorobenzotrifluoride fed as starting material).

Example 12

The procedure for Example 7 was carried out on a 2.5-fold scale and 450.1 g of the resulting oil phase was washed twice with a 10 wt % saline solution and subjected to vacuum concentration. This oil phase was subjected to vacuum distillation (degree of decompression 3.3 to 2.0 kPa, distillation temperature 101° C. to 105° C.) and as a result, 1-cyclopentyl-2-(trifluoromethyl)benzene having a GC purity 99.5%, which was determined by gas chromatographic analysis, was obtained with a total yield of 63.8% (on the basis of o-chlorobenzotrifluoride as starting material).

Example 13

In the procedure carried out in Example 7, except for adding 39.1 g of cyclohexyl bromide (1.2 moles per mole of o-chlorobenzotrifluoride, manufactured by Wako Pure Chemical Industries, Ltd.) instead of 35.8 g of cyclopentyl bromide (1.2 moles per mole of o-chlorobenzotrifluoride, manufactured by Wako Pure Chemical Industries, Ltd.), the same reaction procedure as in Example 7 was carried out.

The oil phase obtained was analyzed by gas chromatography, and results showed that the reaction yield of 1-cyclohexyl-2-(trifluoromethyl)benzene was 72.9% (on the basis of o-chlorobenzotrifluoride fed as starting material).

Example 14

In the procedure carried out in Example 8, except for adding 39.1 g of cyclohexyl bromide (1.2 moles per mole of o-chlorobenzotrifluoride, manufactured by Wako Pure Chemical Industries, Ltd.) instead of 35.8 g of cyclopentyl bromide (1.2 moles per mole of o-chlorobenzotrifluoride, manufactured by Wako Pure Chemical Industries, Ltd.), the same reaction procedure as in Example 8 was carried out.

The oil phase obtained was analyzed by gas chromatography, and results showed that the reaction yield of 1-cyclohexyl-2-(trifluoromethyl)benzene was 75.2% (on the basis of o-chlorobenzotrifluoride fed as starting material).

Example 15

In the procedure carried out in Example 14, except for adding 27 ml (2.7 moles per mole of ferric chloride), instead of 53 ml of a 1M THF solution of ethyl magnesium bromide, the same procedure as in Example 14 was carried out.

The oil phase obtained was analyzed by gas chromatography, and results showed that the reaction yield of 1-cyclohexyl-2-(trifluoromethyl)benzene was 79.4% (on the basis of o-chlorobenzotrifluoride fed as starting material).

Example 16

The procedure for Example 13 was carried out on a 2.5-fold scale and 461.3 g of the resulting oil phase was washed twice with a 10 wt % saline solution and subjected to vacuum concentration. This oil phase was subjected to vacuum distillation (degree of decompression 3.3 to 2.0 kPa, distillation temperature 105° C. to 110° C.) and as a result, 1-cyclohexyl-2-(trifluoromethyl)benzene having a GC purity 98.0%, which was determined by gas chromatographic analysis, was obtained with a total yield of 61.3% (on the basis of o-chlorobenzotrifluoride as starting material).

The invention claimed is:

1. A method of producing cycloalkyl(trifluoromethyl) benzene comprising:
    reacting a halogen-substituted trifluoromethyl benzene as represented by general formula (1) with magnesium metal to produce a Grignard reagent,
    treating 1) an iron salt selected from the group consisting of ferrous chloride, ferric chloride, iron acetate, and iron acetylacetonate or 2) a cobalt salt selected from the group consisting of cobalt chloride and cobalt acetylacetonate with a reducing agent selected from the group consisting of lithium aluminum hydride, sodium boron hydride, sulfites, hydrazine, diisobutylaluminum hydride, oxalic acid, formic acid, and Grignard reagents having 1 to 4 carbon atoms, and
    cross-coupling the Grignard reagent with a cycloalkyl halide in the presence of the iron salt or the cobalt salt at a reaction temperature of 60° C. to 80° C. to produce a cycloalkyl(trifluoromethyl)benzene as represented by general formula (2):

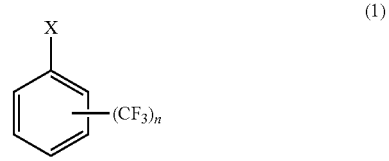
(1)

wherein X is Cl or Br, and n is 1 or 2, and

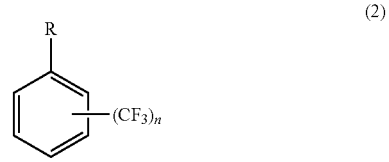
(2)

wherein R is one selected from the group consisting of cyclopropyl, cyclobutyl, cyclopentyl, cyclohexyl, and cycloheptyl, and n is 1 or 2.

2. The method as set forth in claim 1, wherein N-methyl pyrrolidone coexists in the cross-coupling reaction system in which the Grignard reagent is reacted with the cycloalkyl halide in the presence of the iron salt or the cobalt salt.

* * * * *